(12) United States Patent
Calisse et al.

(10) Patent No.: US 7,235,097 B2
(45) Date of Patent: Jun. 26, 2007

(54) APPARATUS FOR A STENT OR OTHER MEDICAL DEVICE HAVING A BISTABLE SPRING CONSTRUCTION

(75) Inventors: Jorge Calisse, Berlin (DE); Petrus A. Besselink, AT Enschede (NL)

(73) Assignee: Paragon Intellectual Properties, LLC, Charleston, WV (US)

( * ) Notice: Subject to any disclaimer, the term of this patent is extended or adjusted under 35 U.S.C. 154(b) by 0 days.

(21) Appl. No.: 10/523,959

(22) PCT Filed: Jul. 29, 2003

(86) PCT No.: PCT/EP03/08384

§ 371 (c)(1),
(2), (4) Date: Nov. 18, 2005

(87) PCT Pub. No.: WO2004/014255

PCT Pub. Date: Feb. 19, 2004

(65) Prior Publication Data
US 2006/0155360 A1    Jul. 13, 2006

Related U.S. Application Data

(60) Provisional application No. 60/402,136, filed on Aug. 7, 2002.

(51) Int. Cl.
*A61F 2/02* (2006.01)
*A61F 2/04* (2006.01)
*A61F 2/06* (2006.01)

(52) U.S. Cl. .................................... 623/1.15; 623/1.16
(58) Field of Classification Search ...... 623/1.11–1.23, 623/1.49–1.54
See application file for complete search history.

(56) References Cited

U.S. PATENT DOCUMENTS 5,861,025 A    1/1999 Sapoval
6,488,702 B1 *  12/2002 Besselink .................. 623/1.15

FOREIGN PATENT DOCUMENTS

EP          1 223 305         7/2002
WO      WO 9832412 A2 *     7/1998

* cited by examiner

Primary Examiner—Glenn K. Dawson
Assistant Examiner—Kathleen Sonnett
(74) Attorney, Agent, or Firm—Franco A. Serafini; Luce, Forward, Hamilton & Scripps LLP (57) ABSTRACT

A stent is described comprising a unit cell having a negative spring rate and a bistable function. The unit cell comprises first and second segments, the first segment being more rigid than the second segment. The second segment is coupled to the first segment, and the first segment comprises a substantially fixed sinusoidal shape. In the contracted state, the second segment is held stable in a sinusoidal shape, but when a force is applied the second segment bends out to a stable, convex-shaped deployed state. The second segments withstand the application of radial forces in the convex-shaped deployed state, and diametral recoil of the stent is minimized.

27 Claims, 6 Drawing Sheets

APPARATUS FOR A STENT OR OTHER MEDICAL DEVICE HAVING A BISTABLE SPRING CONSTRUCTION

FIELD OF THE INVENTION

The present invention relates to stents, and more particularly, to a unit cell of a stent that is configured to snap between contracted and deployed states using a first relatively rigid segment coupled to a second relatively flexible segment.

BACKGROUND OF THE INVENTION

There are several kinds of stents on the market with either balloon expandable or self-expanding function. Balloon expandable stents are generally made from a material that can easily be plastically deformed into two directions. Before insertion, the stent is placed around the balloon section at the distal end of a catheter and pressed together to reduce the outer dimensions.

When the stent is delivered into the body in a desired location, it is expanded and thereby plastically deformed to a larger diameter by inflating the balloon. Once expanded, the stent supports the surrounding tissue and prevents at least local narrowing of the vessel.

Such plastically deformable stents need to have sufficient rigidity in the radial direction, but also some flexibility in the axial direction to enable delivery through tortuous anatomy. Furthermore, the amount of material should be as small as possible and the inner surface of the stent should not obstruct the flow through the channel (e.g., for blood) or cause too much turbulence.

Problems that generally occur after stent implantation are several: After crimping the stent onto the balloon of the delivery catheter, the stent experiences some elastic recoil to a slightly larger diameter, which can cause problems, e.g., snagging, when the catheter is advanced through the patient's vasculature. In addition, the engagement forces between the balloon and stent can become so small that the stent slips off the catheter. Moreover, a large stent delivery profile reduces the number of situations in which the stent can be used.

Another problem with balloon expandable stents is recoil of these stents after deployment. In this case, after expansion by the balloon of the delivery catheter, the stent outer diameter will shrink slightly once the balloon is deflated. The percentage change in deployed stent diameter due to recoil can be as much as 10%, and can cause migration of the stent.

A self-expanding stent typically is made of a more or less elastically expanding structure, which is affixed to the delivery catheter by some external means. For example, this type of stent is held in its constrained state by a delivery sheath that is removed at the moment of stent deployment, so that the stent self-expands to its preferred expanded form. Some of these stents are made of shape memory material with either superelastic behavior or temperature sensitive triggering of the expansion function.

A disadvantage of self-expanding stents is the need for the delivery sheath, thus resulting in a larger delivery profile. The removal of the sheath also requires a sheath retraction mechanism, which has to be activated at the proximal end.

Most balloon expandable and self expanding stents further have the disadvantage of that they experience large length changes during expansion and exhibit a poor hydrodynamic behavior because of the shape of the metal wires or struts.

Still further balloon expandable stents exhibit a positive spring rate, which means that further diametral expansion can only be achieved by higher balloon pressure. Moreover, previously-known stents typically are constructed so that external forces, working on the stent in the radial direction, may cause bending forces on the struts or wires of the structure.

For example, a unit cell of a Palmaz-Schatz stent, as produced by the Cordis division of Johnson & Johnson, or the ACT One Coronary stent, produced by Progressive Angioplasty Systems, Inc. have in their contracted delivery state a flat, rectangular shape and in their expanded condition a more or less diamond-shaped form with almost straight struts (Palmaz-Schatz) or more curved struts (ACT-One).

The shape of the unit cell of such stents is typically symmetrical with four struts each having the same cross section. In addition, the loading of the cell in the axial direction will typically cause an elastic or plastic deformation of all of the struts, resulting in an elongation of the unit cell in the axial direction. These unit cells have a positive spring rate. For stents based upon these unit cells, the stability against radial pressure is merely dependent on the bending strength of the struts and their connections.

In view of these drawbacks of previously known stents, it would be desirable to provide a stent having minimal elastic spring back upon being compressed onto a balloon catheter.

It also would be desirable to provide a stent having minimal recoil so that the stent remains at its selected deployed diameter after expansion.

It further would be desirable to provide a stent having a minimal length change during deployment of the stent.

It still further would be desirable to provide a stent that is not characterized by a positive spring rate, so that achieving further expansion does not require continually increasing balloon pressure.

SUMMARY OF THE INVENTION

In view of the foregoing, it is an object of the present invention to provide a stent having minimal elastic spring back upon being compressed onto a balloon catheter.

It is also an object of the present invention to provide a stent having minimal recoil so that the stent remains at its selected deployed diameter after expansion.

It is another object of the present invention to provide a stent having a minimal length change during deployment of the stent.

It is another object of the present invention to provide a stent that is not characterized by a positive spring rate, so that achieving further expansion does not require continually increasing balloon pressure.

These and other objects of the present invention are achieved by providing a stent comprising a unit cell having a negative spring rate and a bistable function. In the context of the present invention, the phrase "bistable function" means that the unit cell has only two configurations in which it is stable without the need for an external force to hold it in that shape. In a preferred embodiment, the unit cell is formed using at least two different segments, wherein a first segment is relatively rigid while a second segment is more flexible than the first segment.

The first segment preferably comprises a sinusoidal shape and does not substantially change in shape. The second segment is coupled to the first segment in such a way that the first segment inhibits deformation of the second segment in one direction. The second segment has only two stable positions, one in a contracted state and the other in a deployed state.

In the contracted state, the second segment is held stable in a sinusoidal shape when a compressive force is applied against the second segment in a direction toward the first segment. When a radially outward force is applied to the unit cell that is sufficient to displace the sinusoidal profile of the second segment, the second segment will buckle outward from the first segment to a deployed state where it comprises a convex shape. When the second segment is in any other position between the contracted and deployed states it is unstable, and will return to either the contracted or deployed state.

The stent as a whole therefore is deployed when the radially outward force, e.g., provided by a balloon, overcomes the resistance of one or more second segments in one or more unit cells. The expansion of the second segments provides radial expansion of the stent, as the first segments of the unit cells do not substantially change in size or shape.

When a stent comprising the above-described unit cells is deployed to a selected deployed diameter, it reaches its maximum stability against radial pressure. This makes the construction stronger than prior stents because the second segments may withstand considerable radial forces in their stable, convex-shaped deployed states.

Methods of actuating the apparatus of the present invention also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1A:
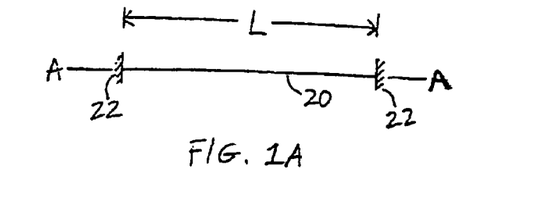
FIGS. 1A–1B show the principle of a bistable mechanism.
Figures 1B, 2:
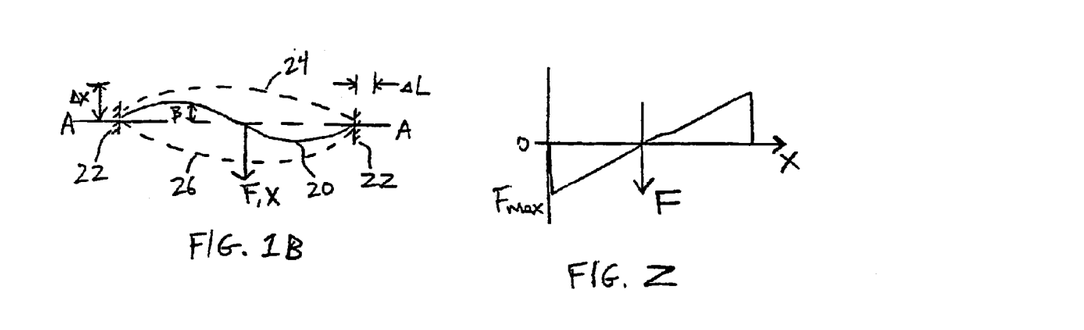
FIG. 2 depicts the force-displacement characteristic of the mechanism of FIG. 1B.

Referring to FIG. 1, the operative principles of the stent of the present invention are described. In FIG. 1A, flexible rod 20 having a length L is affixed at each end by external clamps 22. When flexible rod 20 is compressed along central axis A—A by a distance ΔL, it reaches its buckling stress and the central part of rod 20 then will bend out in a sidewards direction, either to position 24 or 26, as shown in FIG. 1B.

Because the ends of rod 20 are held stable by external clamps 22, it is possible to move the central section of rod 20 between two stable positions 24 and 26. This movement is in a direction X that is perpendicular to central axis A—A of rod 20. All positions between stable positions 24 and 26 are unstable. In FIG. 1B, the central part of rod 20 must be displaced at least a distance Δx before the rod can be transformed from stable position 24 to stable position 26.

FIG. 2 shows the force-displacement characteristics of rod 20 of FIG. 1B. As rod 20 is moved from stable position 24, the force increases rapidly from zero to Fmax. At that moment, rod 20 becomes unstable in a position between stable positions 24 and 26, for example, in the position depicted by the sinusoidal shape of rod 20 in FIG. 1B. At this point, further displacement in direction X requires less force because this spring system has a negative spring rate. The force even becomes zero in the mid position and further movement occurs automatically. As seen in FIG. 2, the system of FIG. 1B is symmetrical and the force needed to move from lower position 26 back to upper position 24 has the same characteristic.

Figures 3, 4:
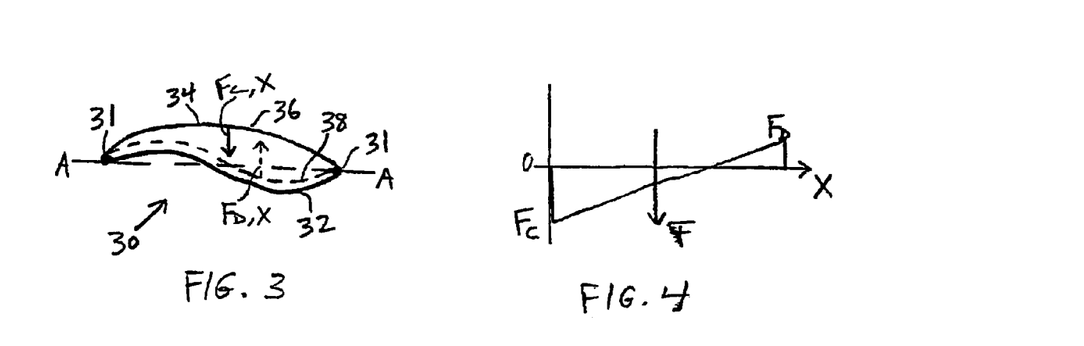
FIG. 3 depicts a bistable unit cell in accordance wits the present invention.
FIG. 4 depicts the force-displacement characteristic of the mechanism of FIG. 3.

Like rod 20 of FIG. 1B, when the ends of second segment 34 are held stable by hinges 31, it is possible to move the central section of second segment 34 between two stable positions 36 and 38 (shown in dotted line in FIG. 3) . The movement occurs in a direction X that is perpendicular to central axis A—A, and all positions between stable positions 36 and 38 are unstable. Second segment 34 is held stable in lower position 38 because it adapts to the sinusoidal profile of first segment 32 when compressed, and is clamped in that position by the compressive forces exerted by coupling each end of second segment 32 to hinges 31.

Like rod 20 of FIG. LB, when the ends of second segment 34 are held stable by hinges 31, it is possible to move the central section of second segment 34 between two stable positions 36 and 38 (shown in dotted line in FIG. 3). The movement occurs in a direction X that is perpendicular to central axis A—A, and all positions between stable positions 36 and 38 are unstable. Second segment 34 is held stable in lower position 38 because it adapts to the sinusoidal profile of first segment 32 when compressed, and is clamped in that position by the compressive forces exerted by coupling each end of second segment 32 to hinges 31.

With respect to FIG. 4, second segment 34 displays an asymmetric force-displacement characteristic. To initially displace second segment 34 from stable upper position 36 requires a compressive starting force $F_C$. To displace second segment 34 from stable lower position 38 requires deployment force $F_D$, which may be less than force $F_C$. Deployment force $F_D$ may be made as small as desired, even zero or negative, but needs to have a positive value if lower position 38 is to be stable.

The application of forces $F_C$ and $F_D$ serve to transform second segment 34 between stable contracted and deployed states. The force required to transform second segment 34 between its two stable states defines the force-displacement characteristic of unit cell 30. As will be described hereinbelow, a stent having a plurality of unit cells 30 may have different force-displacement characteristics for each individual unit cell, to selectively deploy certain unit cells while others remain contracted.

First segment 32 of FIG. 3 preferably has a larger cross-section than second segment 34 so that it is more rigid. Alternatively, instead of using segments of different cross-section, the two segments in each unit cell 30 may have the same cross-sections but exhibit different strengths or rigidity and still accomplish the same effect. One way to obtain such differences in strength or rigidity would be to use different materials for the segments. Another way would be to use the same material, such as a metal, for all the segments but selectively strengthen (e.g., by heat treating) first segment 32.

It should be noted that heat treatment will not strengthen all materials. Nitinol, for example, becomes more pliable as a result of heat treatment. This property of Nitinol can be exploited, however, to render one section of Nitinol more pliable relative to a second, non-heat-treated section of Nitinol.

There are several ways to manufacture unit cell 30 of a stent of the present invention. The device may be manufactured from an arrangement of wire or strip, welded together at specific places, e.g., hinges 31. Alternatively, metal may be deposited in the desired pattern onto a substrate or prealloy powder may be sintered. Alternatively, the device may comprises a tubular material, and a pattern of slits or slots may be made in the wall by means of etching, grinding, cutting (e.g., with a laser, water, etc.), spark erosion or any other suitable method. The pattern also may be made formed as a flat plate and teen welded, brazed or crimped to a more or less cylindrical shape or a cylindrical mid section with two conical ends of enlarged diameter.

Materials that may be used to construct a stent comprising unit cell 30 include polymers, composites, conventional metals and shape memory alloys with superelastic behavior or with temperature sensitive behavior, or a combination of two or more of these materials.

With respect to FIG. 5, a preferred arrangement of two adjacent unit cells in accordance with the present invention is described, wherein horizontal line A—A is parallel to the central axis of a stent. A first unit cell comprises first segment 50 and second segment 40, while the second adjacent unit cell comprises second segment 42 and first segment 52. Second segments 40 and 42 are more flexible than first segments 50 and 52, respectively, and second segments 40 and 42 are coupled to their respective first segments at hinges 46.

Figure 5A:
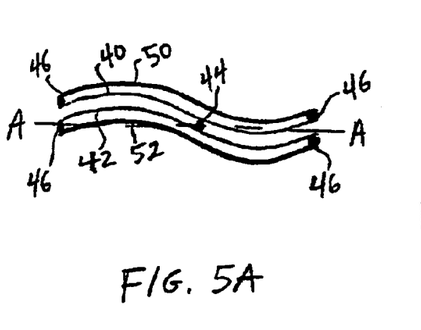
FIGS. 5A–5B shows two adjacent unit cells in accordance with the present invention in contracted and deployed states, respectively.

These adjacent unit cells preferably are arranged so that second segments 40 and 42 are disposed between first segments 50 and 52, as shown in FIG. 5A. Second segments 40 and 42 preferably are connected by joint 44 that is disposed near a midpoint of second segments 40 and 42. In FIG. 5A, the sinusoidal configurations of rigid first segments 50 and 52 serve to hold flexible second segments 40 and 42 in stable, sinusoidally-shaped contracted states.

Figure 5B:
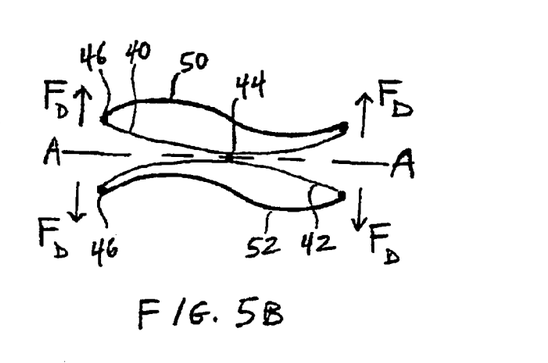

Referring to FIG. 5B, the adjacent unit cells of FIG. 5A are depicted in a stable deployed state. The unit cells preferably are deployed by applying uniform radially outward force $F_D$, e.g., by inflating a balloon, that is sufficient to overcome the resistance of second segments 40 and 42 in their stable, sinusoidal-shaped contracted states. Once force $F_D$ has overcome this resistance, second segments 40 and 42 will automatically snap into their respective stable, convex-shaped deployed positions, as shown in FIG. 5B.

Figure 6:
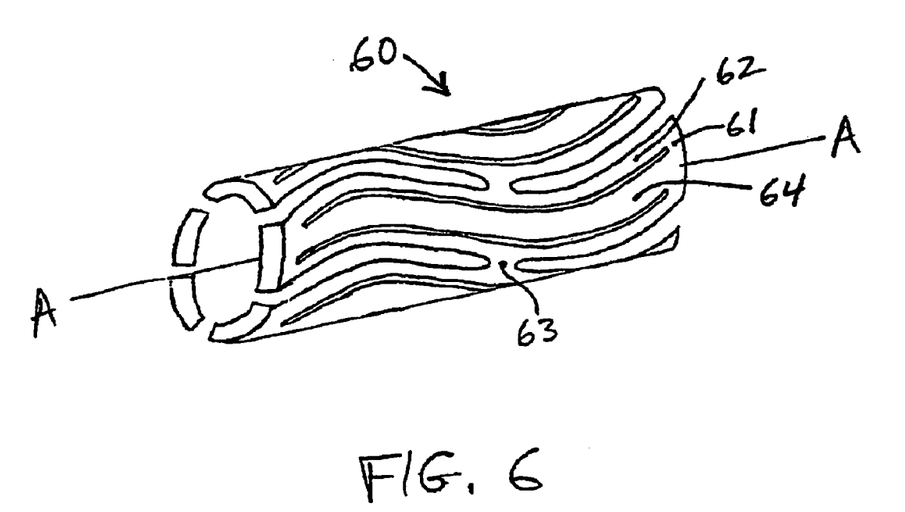
FIG. 6 shows a single circumferential ring of unit cells of a stent in a stable, fully collapsed configuration.
Figure 7:
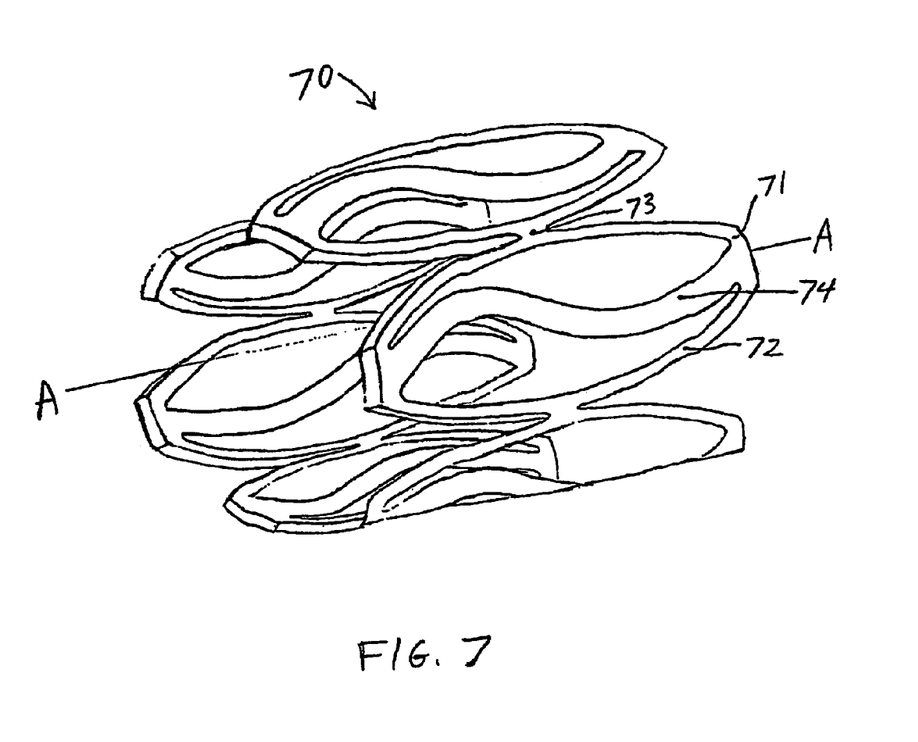
FIG. 7 shows the circumferential ring of unit cells of FIG. 6 in a stable, fully expanded configuration.

FIG. 6 shows the general appearance of a circumferential ring of a tubular stent constructed in accordance with the present invention in its fully contracted configuration. Ring 60 comprises a plurality of unit cells, each unit cell comprising second segment 62 that is more flexible than first segment 64. First and second segments 64 and 62 are coupled together by flexible hinges 61, while adjacent second segments are connected by joints 63. In FIG. 7, circumferential ring 70 of an illustrative stent is shown in a fully deployed state. Second segments 72 of ring 70 have been deployed and assume stable, convex shapes. Second segments 72 provide the radial expansion of ring 70, while first segments 74 substantially maintain their original shapes. Hinges 71 of FIG. 7 couple first and second segments 74 and 72, while joints 73 connect adjacent second segments 72.

Referring to FIG. 8, stent 80 constructed of a series of three circumferential rings 60 is depicted, for illustrative purposes, flattened. In three-dimensions, stent 80 would extend circumferentially abort central axis A—A to form an extended tubular shape similar to comprising a series of circumferential rings as depicted in FIGS. 6–7, such that segments 100 and 103 of stent 80 are in effect the same segment.

Figure 8A:
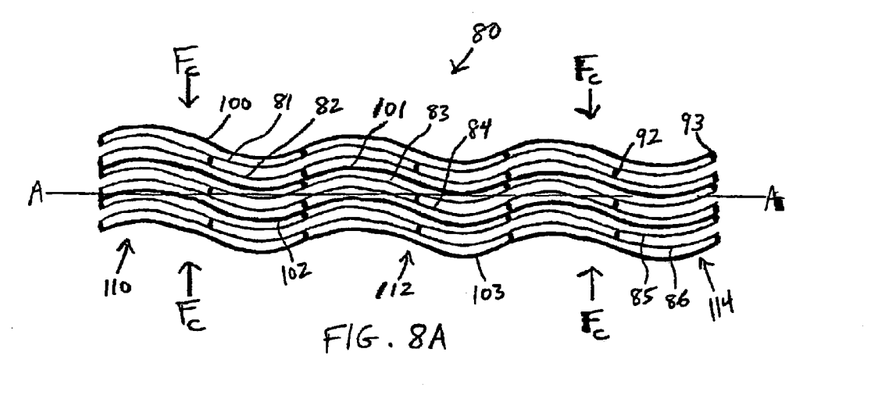
FIGS. 8A–8B depicts features of a plurality of unit cells in accordance with the present invention in contracted and deployed states, respectively.

In FIG. 8A, stent 80 is illustrated in a contracted state. Stent 80 comprises first segments 100, 101, 102 and 103, and further comprises second segments 81, 82, 83, 84, 85 and 86 that are more flexible than first segments 100–103. First segments 100–103 substantially maintain their original shape. There preferably are two second segments disposed between every two first segments, as depicted in FIG. 8A. Joints 92 connect adjacent second segments, while hinges 93 connect first and second segments. Joints 92 and hinges 93 are disposed at approximately the same distance apart as they longitudinally alternate along axis A—A.

Stent 80 is contracted by applying a compressive force $F_C$, e.g., the force applied by the fingers of a physician, as shown in FIG. 8A. Compressive force $F_C$ contracts second segments 81 and 82 into stable, sinusoidal shapes between first segments 100 and 101. Compressive force $F_C$ also contracts second segments 83 and 84 into stable, sinusoidal shapes between first segments 101 and 102, and further contracts second segments 85 and 86 into stable, sinusoidal shapes between first segments 102 and 103.

Figure 8B:
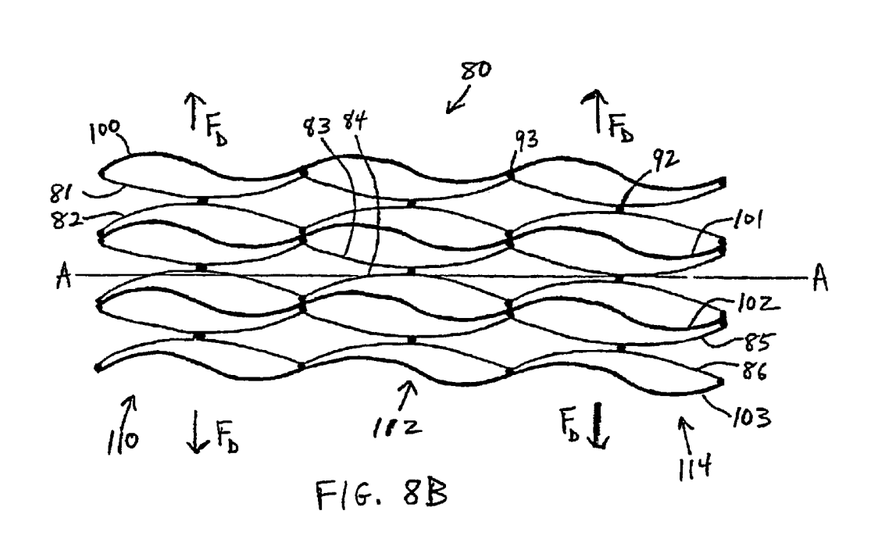

The resistive force that second segments 81–86 provide in their stable, sinusoidal-shaped contracted state may be overcome by radially outward force $F_D$, which is perpendicular to axis A—A, as shown in FIG. 8B. Second segments 81–86 snap from their contracted states to stable, convex-shaped deployed states when force $F_D$ is applied, as shown in FIG. 8B.

Figure 9A:
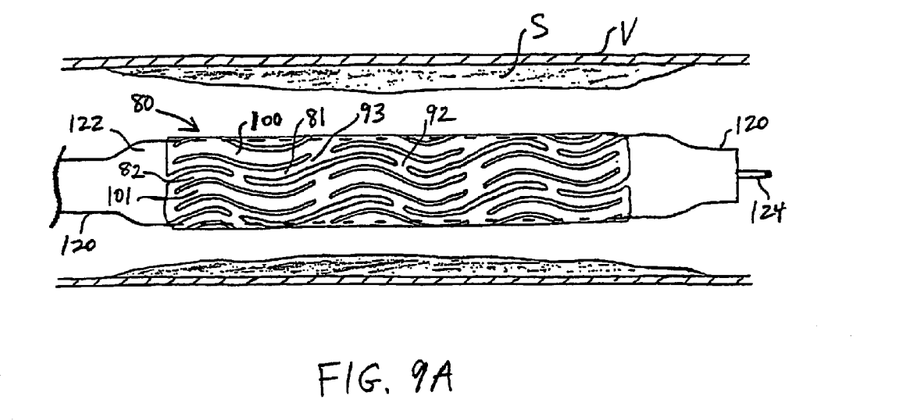
FIGS. 9A–9B describe a preferred method of using a stent in accordance with the present invention.
Figure 9B:
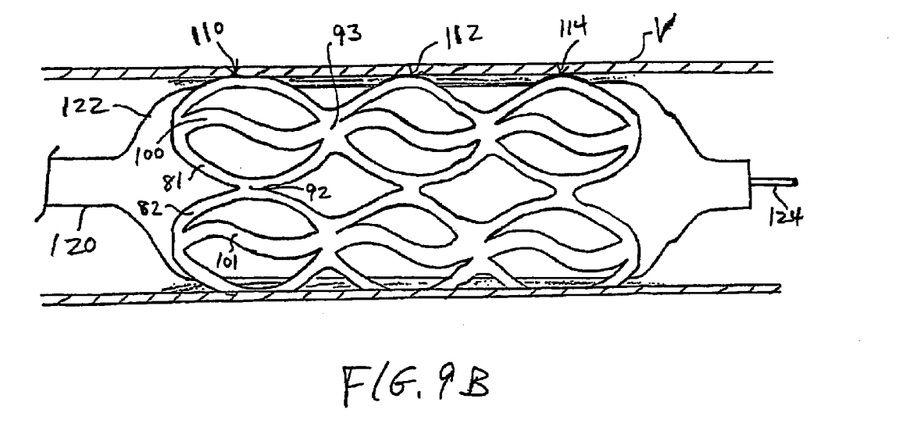

Referring now to FIG. 9, arm exemplary method of using stent 80 of FIGS. 8A–8B is described. In FIGS. 9A–9B, it should be noted that stent 80 is illustratively depicted from a side view as having a preferred geometry and thickness, whereas the same stent in FIGS. 8A–8B was depicted as flattened for illustrative purposes.

In a first method step shown in FIG. 9A, stent 80 is compressed onto balloon 122 of conventional balloon catheter 120, e.g., by applying a compressive force manually. Catheter 120 is inserted into a patient's vessel, preferably over guidewire 124, and a distal region of catheter 120 having balloon 122 is positioned within treatment vessel V. The distal region of catheter 120 preferably is positioned under fluoroscopy using at least one radiopaque marker band (not shown) disposed on the distal region of catheter 120.

When catheter 120 is properly positioned, e.g., within stenosed region S, balloon 122 is inflated to cause one or more second segments 81–86 to deploy to a convex shape bowed away from first segments 100–103, as shown in FIG. 9B. Specifically, balloon 122 provides a radially outward force, described hereinabove with respect to FIG. 8B, that overcomes the resistive force provided by one or more second segments 81–86 in the contracted state. Having flexible second segments 81–86 snap into expanded stable positions provides a stent with an extremely rigid surface at all diameters that is able to better withstand external forces than previously known stents.

The flexibility of stent 80 may be increased by disconnecting several unit cells from their neighbor unit cells, for example, by cutting the center of one or more hinges 93. Another way to increase flexibility is to change the geometry of various segments within selected unit cells along axis A—A. In other words, referring to FIG. 8B, one or more second segments 81–86 could be constructed with larger and smaller diameter (or otherwise flexible and rigid) segments that alternate after each hinge 93. In addition, varying the properties of second segments 81–86 in one or more selected unit cells, e.g., increasing or decreasing the deployment force for specific unit cells, stent 80 may be made capable of attaining different diameters in the deployed state, depending on the amount and location of unit cells that are transformed to the deployed state.

Stent 80 may achieve a range of diameters by deploying selected unit cells in a stepwise fashion. In one scenario, the diameter of stent 80 may be increased incrementally by varying the properties of second segments 81–86 to cause some rows of the stent to expand preferentially before other rows. For example, as balloon 122 is inflated at a relatively low balloon pressure, only unit cells in the row of second segment 81 will deploy. Then, as balloon 122 further is inflated, only those unit cells in the row of second segment 82 nay deploy for a somewhat higher balloon pressure, and so forth, until the desired number of rows have been deployed to achieve the desired stent diameter. In this manner, stent 80 may be suitable for use in a wide range of vessels.

Furthermore, stent 80 may comprise different external diameters along its length to conform to particular cavities. This is achieved by varying the properties of second segments 81–86 along central axis A—A of stent 80. For example, hinges 93 may be used to divide stent 80 into a plurality of distinct sections, e.g., first end 110, second end 114 and intermediate section 112. The unit cells within first end 110 comprise second segments 81 and 82 that exhibit a first force-displacement characteristic. The unit cells within second end 114 may comprise second segments 85 and 86 that exhibit second force-displacement characteristics, while the unit cells within intermediate section 112 comprise second segments 83 and 84 having yet different force-displacement characteristics.

The force-displacement characteristics of each unit cell may be tailored, for example, such that second segments 81 and 82 may easily deploy with little balloon pressure, while second segments 83–86 do not deploy for such balloon pressure. This provides stent 80 having a deployed first end 110 and contracted intermediate section 112 and second end 114. To provide a progressively smaller, stent, second segment 83 may be configured to deploy within intermediate section 112 while second segment 84 is not configured to deploy when the same force is applied. This provides partial deployment within intermediate section 112 and provides an intermediate diameter. Alternatively, all unit cells within first end 110 and second end 114 may be deployed while unit cells within intermediate section 112 remain partially or fully contracted to provide a generally hourglass-shaped stent along axis A—A.

The above examples describe a few variations in stent configurations by varying the force-displacement characteristics of individual unit cells. The present invention is intended to cover the numerous other stent configurations that can be attained when the unit cells selectively deploy as particular forces are applied.

Additionally, the overall stent diameter in the deployed state further may be varied by providing first and second segments having different lengths, because relatively long second segments may bow away from their respective first segments a greater distance than smaller second segments. Also, stent characteristics may be varied when certain sections of the stent comprise a different number of unit cells relative to other sections.

The invention claimed is:

1. An expandable tubular member comprising a plurality of unit cells, each unit cell comprising a first segment having proximal and distal ends and a substantially sinusoidal shape, and a second segment having proximal and distal ends, the proximal end of the first segment being coupled to the proximal end of the second segment, the distal end of the first segment being coupled to the distal end of the second segment, the second segment being more flexible than the first segment, wherein the unit cell has a stable contracted state in which the second segment substantially conforms to the sinusoidal shape of the first segment, and a deployed state in which the second segment has a convex shape bowed away from the first segment, wherein around a circumference of the expandable tubular member, two second segments are disposed between every two first segments and coupled directly to one another.

2. The expandable tubular member of claim 1 wherein the second segment of each unit cell is coupled to the first segment so that the first segment inhibits deformation of the second segment in the contracted state.

3. The expandable tubular member of claim 1 wherein the second segment of each unit cell is stable only in the contracted and deployed states.

4. The expandable tubular member of claim 1 wherein the first segment of each unit cell is substantially rigid.

5. The expandable tubular member of claim 1 wherein the first segment of each unit cell comprises a larger cross sectional area than the second segment.

6. The expandable tubular member of claim 1 wherein the first and second segments of each unit cell are manufactured using different materials.

7. The expandable tubular member of claim 1 wherein the proximal and distal ends of the first and second segments of each unit cell are coupled together by hinges.

8. The expandable tubular member of claim 7 wherein the hinges of each unit cell are elastic hinges.

9. The expandable tubular member of claim 7 wherein the hinges of each unit cell are plastic hinges.

10. The expandable tubular member of claim 1 wherein the unit cells are transformed from the contracted state to the deployed state by application of a uniform radially outwardly directed force to an interior surface of the expandable tubular member.

11. The expandable tubular member of claim 1 wherein a first subset of the plurality of unit cells has a second segment with a first cross-sectional area and a second subset of the plurality of unit cells has a second segment with a second cross-sectional area.

12. The expandable tubular member of claim 1 wherein the plurality of unit cells are arranged in a longitudinally arranged series of circumferential rings.

13. The expandable tubular member of claim 1 wherein the expandable tubular member is capable of attaining different outer diameters depending on the amount and location of unit cells that are transformed to the deployed state.

14. The expandable tubular member of claim 1 wherein the unit cells are designed and arranged to provide a range of diameters for the expandable tubular member in a stepwise fashion.

15. The expandable tubular member of claim 14 wherein the expandable tubular member has an initial diameter at a first end, a final diameter at a second end, and at least one intermediate diameter between the first and second ends, the intermediate diameter differing from the initial and final diameters.

16. The expandable tubular member of claim 15 wherein the initial and final diameters are the same.

17. The expandable tubular member of claim 12 wherein within a circumferential ring, a first subset of unit cells has a different force-displacement characteristic than a second subset of the plurality of unit cells.

18. The expandable tubular member of claim 1 wherein the second segment of each unit cell is coupled to the second segment of an adjacent cell by a joint disposed near a midpoint of the second segments.

19. The expandable tubular member of claim 1 wherein the expandable tubular member is made from a polymer, a metal, a composite, a shape memory material with superelastic behavior, a shape memory material with temperature sensitive behavior, or a combination of two or more of these materials.

20. A method for deploying an expandable tubular member having two substantially stable states, the method comprising:
providing an expandable tubular member comprising a plurality of unit cells in a contracted state, wherein each unit cell comprises a first segment having proximal and distal ends and a substantially sinusoidal shape, and second segment having proximal end that is coupled to the proximal end of the first segment and distal end that is coupled to the distal end of the first segment, the second segment being more flexible than the first segment, wherein the second segment substantially conforms to the sinusoidal shape of the first segment in the contracted state, wherein around a circumference of the expandable tubular member, two second segments are disposed between every two first segments and coupled directly to one another; and
deploying at least one of the unit cells of the expandable tubular member by causing the second segment of the unit cell to deploy to a convex shape bowed away from the first segment of the unit cell.

21. The method of claim 20 wherein the expandable tubular member is provided in the contracted state by compressing the expandable tubular member onto a delivery device.

22. The method of claim 21 wherein at least one unit cell is deployed by applying a radially outward force by expanding the delivery device.

23. The method of claim 20 wherein unit cells of the expandable tubular member are deployed in a stepwise fashion.

24. The method of claim 20 wherein the number of unit cells that are deployed is proportionate to a radially outward force that is applied to the expandable tubular member.

25. The method of claim 20 wherein unit cells are selectively deployed by providing second segments having varying diameters.

26. The method of claim 20 wherein the diameter of the expandable tubular member in a deployed state is varied by varying lengths of first and second segments of a unit cell.

27. The method of claim 20 wherein the diameter of the expandable tubular member in a deployed state is varied by varying the number of unit cells that are provided in the contracted state.

* * * * *